United States Patent [19]
Chmielewska et al.

[11] Patent Number: 6,069,234
[45] Date of Patent: May 30, 2000

[54] MODIFIED COAGULATION AGENT

[75] Inventors: Joanna Chmielewska, Stockholm; Tomas Lundqvist, Göteborg; Erifili Masialou; Derek Ogg, both of Stockholm, all of Sweden

[73] Assignee: Pharmacia & Upjohn AB, Stockholm, Sweden

[21] Appl. No.: 08/994,328

[22] Filed: Dec. 19, 1997

[30]     Foreign Application Priority Data

Dec. 20, 1996 [SE] Sweden ................................. 9604744

[51] Int. Cl.$^7$ ...................... A61K 37/547; A61K 37/02; C12N 15/01; C07K 13/00

[52] U.S. Cl. ..................... 530/381; 424/84.64; 435/68.6; 530/380

[58] Field of Search ................................. 530/381, 380

[56]                 References Cited

FOREIGN PATENT DOCUMENTS 0 540 051   10/1992   European Pat. Off. .

OTHER PUBLICATIONS

Persson et al. J. Biol. Chemistry, 266(4), 2453–2458, Apr. 1991.

Chemical Abstracts, vol. 92, No. 9, Mar. 3, 1980 (Mar. 3, 1980), (Columbus, Ohio, USA), Mortia, Takashi et al, "Structural and functional characteristics of a proteolytically modified, Gla domain–less bovine factor X and Xa (des light chain residues 1–44)", pp. 124–128, The Abstract No. 71347k, Proc. Steenbock Symp. J. 1980, 124–128.

Chemical Abstracts, vol. 122, No. 13, Mar. 27, 1995 (Mar. 27, 1995), (Columbus, Ohio, USA), Donath, Marie–Jose S.H. et al, "The role of cleavage of the light chain at positions Arg1689 or Arg1721 in subunit interaction and activation of human blood coagulation factor VIII", p. 657, The Abstract No. 157118e, J. Biol. Chem. 1995, 270 (8), 3648–3655.

Chemical Abstracts, vol. 100, No. 17, Apr. 23, 1984 (Apr. 4, 1984), (Columbus, Ohio, USA), Skogen, William F. et al, "Comparison of coagulation factor Xa and des–(1–=44)factor Xa in the assembly of prothrombinase", p. 302, The Abstract No. 135005j, J. Biol. Chem. 1984, 259(4), 2306–2310.

J. Hauptmann, et al. "Synthetic Inhibitors of Serine Proteinases XVI, Influence of 3– and 4–Amidinobenxyl Derivatives on the Formation and Action of Thrombin" *Thrombosis Research*, (1978) vol. 12, No. 5 pp. 735–744.

J. Sturzebecher, et al. "Synthetic Inhibitors of Serine Proteinases XIV,+) Inhibition of Factor Xa by Derivatives of Benzamidine" *Thrombosis Research*, (1976) vol. 9, pp. 637–646.

Masahide Yamazaki, "Factor Xa Inhibitors" *Drugs of the Future* (1995); 20(9):pp. 911–918.

J. E. Folk, Carboxypeptidase B (Porcine Pancreas) *Methods in Enzymology* (1970) vol. 19. pp. 504–509.

R.R. Tidwell, et al. "Strategies for Anticoagulation with Synthetic Protease Inhibitors. Xa Inhibitors Versus Thrombin Inhibitors" *Thrombosis Research*, (1980) vol. 19. pp. 339–349.

P.T. Turkington. "Degradation of Human Factor X by Human Polymorphonuclear Leucocyte Cathepsin G and Elastase" *Haemostasis* (1991) vol. 21, pp. 11–116.

K. Padmanabhan, et al. "Structure of Human Des(1–45) Factor Xa at 2·2 Å Resolution" *J. Mol. Biol.* (1993) vol. 232, pp. 947–966.

Milton T. Stubbs, et al. "Crystal structures of Factor Xa Specific Inhibitors in Complex with Trypsin: Structural Grounds for Inhibition of Factor Xa and Selectivity Against Thrombin" *FEBS Letters,* (1995) vol. 375, pp. 103–107.

Hans Brandstetter, et al. "X–Ray Structure of Active Site–inhibited Clotting Factor Xa" *The Journal of Biological Chemistry,* (1996) vol. 271, No. 47. pp. 29988–29992.

International Search Report.

Chemical Abstracts, vol. 126, No. 1, Jan. 6, 1997 (Jan. 1, 1997), (Columbus, Ohio, USA), J. Biol. chem., "X–ray structure of active site–inhibited clotting factor Xa. Implications for drug design and substrate recognition", p. 430, The Abstracts No. 3740x, Brandstetter, Hans, et al., 1996, 271 (47), 29988–29992.

Chemical Abstracts, vol. 124, No. 7, Feb. 12, 1996 (Feb. 12, 1996), (Columbus, Ohio, USA), Stubbs, Milton T., et al, "Crystal structures of factor Xa specific inhibitors in complex with trypsin: structural grounds for inhibition of factor Xa and selectivity against thrombin", p. 620, The Abstract No. 80557d, FEBS Lett. 1995, 375 (1,2) 103–107.

Chemical Abstracts, vol. 119, No. 20, Nov. 15, 1993 (Nov. 11, 1993), (Columbus, Ohio, USA), Padmanabhan, Kaillathe et al., "Structure of human Des (1–45) factor Xa at 2.2 A resolution", p. 445, The Abstract No. 220485c, J. Mol. Bio. 1993, 232 (3), 947–966.

*Primary Examiner*—Cecilia J. Tsang
*Assistant Examiner*—Michael Borin
*Attorney, Agent, or Firm*—Gilberto M. Villacorta; Pepper Hamilton LLP

[57]                 ABSTRACT

The present invention is directed to a modified coagulation factor Xa which has an improved capacity of forming crystals compared to its native form. Such crystals or crystalline composition are especially useful for studies in crystalline form of the active catalytic site of factor Xa when it is complexed to a specific affinity ligand with inhibiting characteristics.

14 Claims, 2 Drawing Sheets

MODIFIED COAGULATION AGENT

FIELD OF INVENTION

The present invention relates to modified human factor Xa with a specifically truncated light chain which has an improved capacity of forming crystals suitable for crystallographic studies with specific affinity ligands.

BACKGROUND OF THE INVENTION

Some of the most wide-spread and powerful antithrombotic agents used in therapy are heparins and low molecular weigh active fragments of heparins. These agents have general drawbacks in their requirement of parenteral administration for therapeutic efficacy and in their rather unspecified anticoagulant activity. In the development of novel antithrombotic agents it is therefor highly desirable to find selective inhibitors of coagulation factors available with oral administration, e.g. low molecular weight compounds with a high biologic specificity. Initial efforts in field were directed to find inhibitors to thrombin, but since such inhibition might have clinical drawbacks, subsequent efforts have been directed towards the serine protease factor Xa, the enzyme directly responsible for thrombin activation. Factor Xa is an especially desirable target for the design of selective inhibitors in the development of anticoagulant drugs, since the two branches of the coagulation cascade (the intrinsic and extrinsic pathways) converge on this agent. A number of inhibitors of factor Xa are documented in the literature, such as the compound DX9065a and its analogues disclosed in EP 0 540 051 to Daiichi, which are selective to factor Xa compared to thrombin. For a review of synthetic factor Xa inhibitors, it is referred to Drugs of the Future, 1995, Vol. 20, No. 9, pp. 911–918: M Yamazaki. The structure of factor Xa is thoroughly discussed in J. Mol. Biol., 1993, Vol. 232, pages 947–66: K Padmanabhan et al, where it is confirmed that it comprises several epidermal growth factor (EGF)-like domains of which one is disordered in crystals. Generally, active factor Xa consists of a light chain comprising the EGF-domains and having a N-terminal region containing gamma-carboxyglutamic acid (Gla)-residues. The light chain is connected to a heavy chain by a disulfide bond and said heavy chain contains a catalytic domain featuring the active site triad of His236, Asp279 and Ser376 which has a high degree of similarity to other trypsine-like serine proteases. In this article, it is also reported certain difficulties to crystallize factor Xa inhibited with dansyl-Glu-Gly-Arg chloromethyl ketone (DEGR) possibly due to interactions of the C-terminal of the light chain and the active site. Also, in FEBS Letters, 1995, Vol. 375, pages 103–7: MT Stubbs et al., the difficulties in obtaining crystals of factor Xa for inhibition studies are acknowledged. The authors of this article have therefore instead attempted to investigate the binding of selected factor Xa inhibitors to the active site of trypsine to obtain structural information of the binding site for the inhibition of factor Xa. The coordinates from binding of DX9065a to trypsine are transferred to factor Xa, whereupon its hypothetical interaction with Factor Xa could be more closely studied. The recently published article in the Journ. of Biol. Chem. 1996, Vol. 271 (47), pp. 29988–92: H Brandsetter et al., discloses crystal structures of factor Xa deprived of the amino acids L1 –L44 (des-Gla-fXa) in complex with the previously mentioned inhibitor DX-9065a.

It would obviously constitute a major advantage to make factor Xa more available for inhibition studies in crystalline form in an with a retained active site, so a powerful model for designing inhibition candidates is obtained.

DESCRIPTION OF THE INVENTION

It is the object of the present invention is to provide a modified factor Xa which can be used in crystalline form for inhibition studies.

Another object of the present invention is provide a method of enzymatically preparing a modified factor Xa, suitable for inhibition studies in crystalline form.

Still another object of the present invention is to provide crystalline forms of factor Xa both, with and without an inhibiting agent bound to its active site.

A further object of the present invention is to employ the modified factor Xa in crystalline form in methods for designing novel antithrombotic drugs.

The present invention is directed to a modified factor Xa, in particular human factor Xa, which has an improved capacity of forming crystals compared to its native forms. The inventive modified factor Xa has a capacity of forming crystals both together with an agent which inhibits its protease activity while acting as an affinity ligand and without the presence of any molecule which can act as an affinity ligand. Such crystals or crystalline composition are especially useful for studies the active catalytic site of factor Xa bound to a specific affinity ligand with inhibiting characteristics. These types of studies aim to find candidate compounds with factor Xa protease inhibitory activity with enhanced affinity and specificity, in order to provide new improved drug candidate molecules with antithrombotic activity.

The modified factor Xa, according to the present invention, generally is described by having the light protein chain of factor Xa truncated in its N-terminal region and in its C-terminal region. The heavy chain connected to the light chain by a single disulfide linkage features the active, catalytic site in its maintained native structure. The modified factor Xa has a light chain with retained epidermal growth factor (EGF)-like domains. Preferably, the light chain of the modified factor Xa is deprived of its N-terminal gamma-carboxyglutamic acid (Gla) containing region. Most preferably it is also deprived of its C-terminal amino acid. A particularly preferred modified factor Xa will have tryptophane (Trp) as the N-terminal amino acid and glutamic acid (Glu) as the C-terminal amino acid of the light chain. The most preferred modified factor Xa according to the present invention has a polypeptide of 40 amino acids removed from the N-terminal end of the light chain and in the C-terminal end the amino acid residue arginine (Arg) is removed.

The invention also is directed to a method of preparing such modified factor Xa by enzymatically cleaving its light chain to remove a fragment in its N-terminal region and a fragment in its C-terminal region. The enzymatic cleaving can be performed by a simultaneous activity of two different enzymes, each having its specific protease activity. According to the inventive method, it is especially preferred that the light chain is cleaved by cathepsin G (EC 3.4.21.20) to remove a fragment in its N-terminal region, as described in Haemostasis, 1991, Vol. 21, pages 111–6: PT Turkington, while the light chain preferably is cleaved by carboxypeptidase B (IUB classification 3.4.2.2) to remove the C-terminal amino acid, as described by JE Folk in Methods of Enzymology, 1970, Vol. 19, pages 504–508. Preferably, a polypeptide of 40 amino acids is removed from the light chain of by cleaving with cathepsin G while C-terminal arginine of the light chain is removed by cleaving with the carboxypeptidase. The present invention is also directed to crystals of a modified factor Xa both without an affinity ligand and in combination with a specific affinity ligand, preferably with inhibiting characteristics when complexed to the active, catalytic site of factor Xa. The inhibitors of factor Xa preferably are low molecular weight heterocyclic compounds or oligopeptides, capable of interaction with the catalytic site. Several types of such compounds are described in the literature: Thromb. Res., 1976, Vol. 9, page 637–646: J Sturzebecker et al., Thromb. Res., 1978, Vol. 12(5), pages 735–744: J Hauptmann, Thromb. Res., 1980, Vol. 19, pages 339–349: RR Tidwell et al. and the previously mentioned Drugs of the Future, 1995, Vol. 20(9), pages 911–918: M Yamazaki which all are incorporated here as references.

The crystals of modified factor Xa and inhibitor can be prepared with methods more closely described, below in Example 2. Alternatively, a solution of an inhibitor can be soaked into the crystal lattice of a crystalline composition of the modified factor Xa to form complexes of protein and inhibitor for further investigation. The modified factor Xa molecules according to present invention admit that crystals may obtained during many different conditions. Especially advantageous is the possibility to admitted by the present invention to perform crystalline studies of fXa and its inhibitors under conditions which more resemble physiological conditions (such as pH and salt concentration). Most importantly, the present invention provides a method for designing antithrombotic drugs characterized by employing the modified factor Xa in a crystalline form in binding studies with selected molecules with potential inhibiting characteristics. It is obvious that the present invention provides a powerful tool for a future drug modeling in the field of antithrombotics.

DETAILED DESCRIPTION OF THE INVENTION

Figure 1:
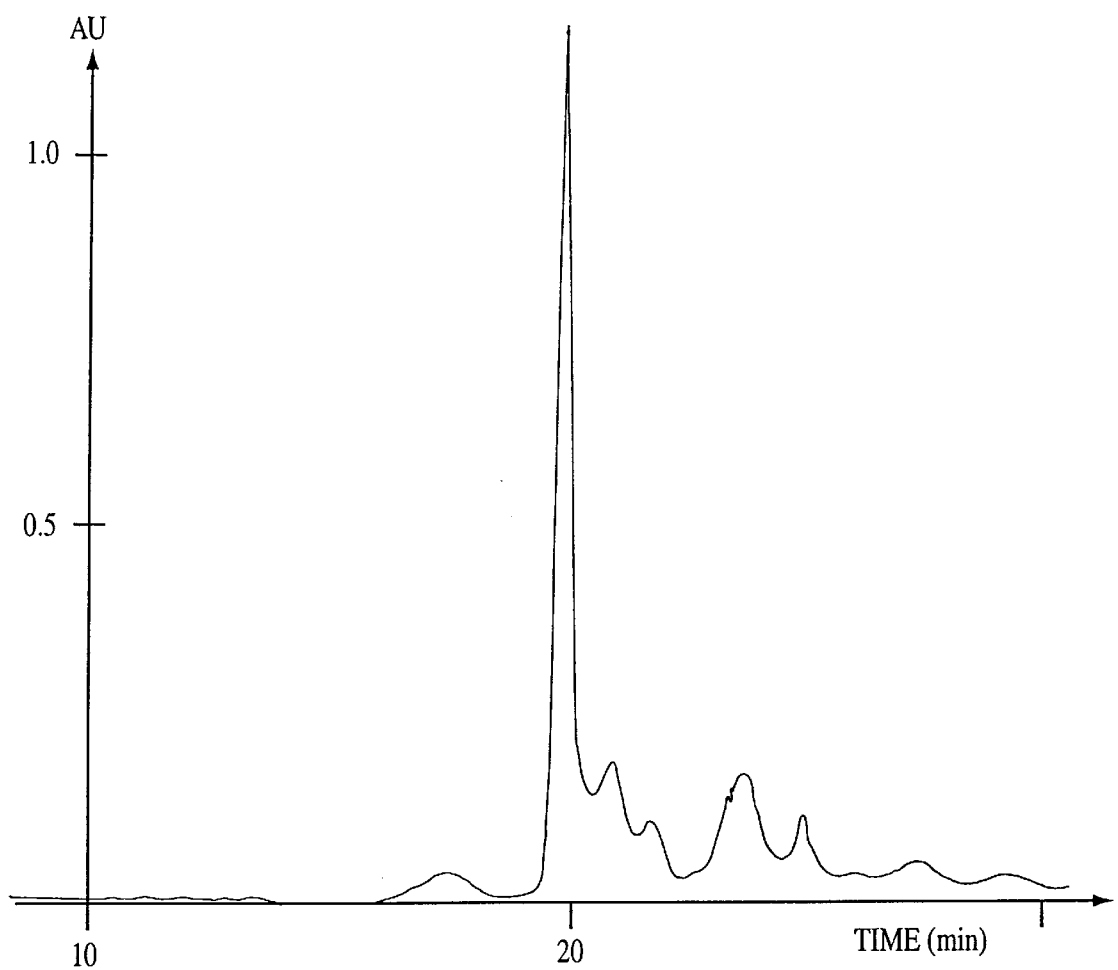

FIG. 1 demonstrates the separation of a factor Xa modified according to the present invention by cathepsin G and carboxypeptidase B was performed by anion exchange chromatography on a mono Q HR 5/5 column.

Figure 2:
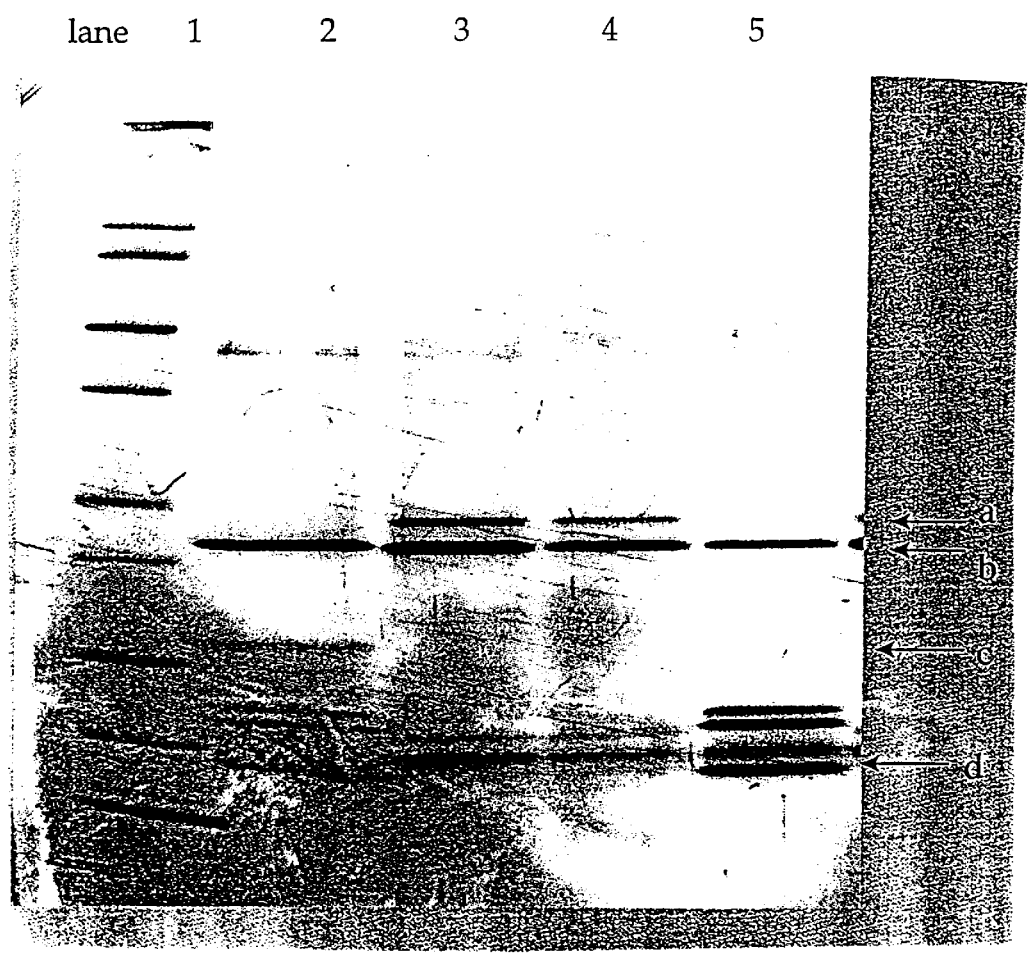

FIG. 2 is a picture of an SDS-PAGE gel demonstrating the effect of cathepsin G and carboxypeptidase B on factor Xa.

EXAMPLE 1

Human factor Xa was incubated at 37° C. for 2 hours with cathepsin G at a protease/protein ratio of 1:500 and with carboxypeptidase B at protease/protein ratio of 1:10 (w/w), in the presence of CHAPS (5 mM) and EDTA (1 mM). Under these conditions maximal removal of the Gla-domain was found to occur. Aliquots were taken at 0, 1 h and 2 h prior to SDS-PAGE. The truncated factor Xa was immediately desalted on a PD-column equilibrated with 20 mM Hepes and 50 mM NaCl pH 8.0. Subsequently, the protein was applied on a mono Q anion exchange column and was thereafter eluted by a linear gradient of 200 mM ammonium sulfate in 20 mM Hepes pH 8.0. The protein fractions were pooled and concentrated by vacuum centrifugation. The concentrated protein was then dialyzed overnight against a buffer comprising 20 mM Hepes pH 8.0 and 50 mM ammonium sulfate.

Factor Xa assay

The amidolytic activity of the truncated factor Xa (2.2 nM) towards Arg-Gly-Arg-paranitroanilide (S-2765, 500 µM) in 50 mM Tris pH 8.0 containing 150 mM NaCl was determined by monitoring the increase in absorbance at 405–490 nm that is due to release of the hydrolysis product of the chromogenic substrate. The assay was carried out at room temperature using a microtiter reader.

SDS-Polyacrylamide gel electrophoresis(PAGE)

The purity of a truncated factor Xa was analyzed by running a 4–20% gradient SDS-page gel under reducing conditions. Following electrophoresis, the bands were visualized by a silver staining method.

Amino acid sequence determination and mass spectroscopy

The amino acid sequence of the truncated factor Xa was determined by automated Edman degradation using a HP G1005A instrument. Approximately 5–6 residues were determined. Electrospray mass spectra was obtained using a pos ESI-FIA on a VG Quattro mass spectrometer. Separation of the truncated factor Xa from cathepsin G and carboxypeptidase B was performed by anion exchange chromatography on a mono Q HR 5/5 column with a flow rate of 1 ml/min, see FIG. 1. As buffers 20 mM Hepes pH 8.0 (buffer A) and buffer A+1 M ammonium sulfate (buffer B) were used and a gradient of 0–20% in 20 ml was employed. The main peak on FIG. 1 (RT 20 min) corresponds to Gla-domainless (-Arg) factor Xa.

N-terminal amino acid sequencing of the protein from the main peak showed two N-terminal sequences, one from the L-chain, starting at position Lys-45 and one from the H-chain, starting at Ile-53, see Table 1. These results verify that the Gla-domain was lost under the applied conditions. The removal of Arg at the C-terminal of the light chain was confirmed by electrospray mass spectra (results not shown).

Referring to FIG. 2 showing SDS-PAGE electrophoresis (in reducing conditions) with 320 ng protein in each well, having molecular mass markers (6–200 kDa) in lane 1; human fXa in lane 2; Human fXa treated with the two enzymes 2 h incubation in lane 3; human fXa treated with two enzymes, after desalting in lane 4 and human fXa treated with the two enzymes after mono Q in lane 5. In FIG. 2, the position for carboxypeptidase is indicated by a, the position for the heavy chain, the light chain and the Gla-domainless light chain of fXa are indicated by b, c and d, respectively. FIG. 2 indicates that the proteolysis by cathepsin G after 2 h incubation, was localized to the light chain of factor Xa, see lane 3. Furthermore, it is evident that completely homogenous protein was not obtained, since the final product was partly degraded, see FIG. 2, compare lanes 4 and 5.

TABLE 1

Amino acid sequence analysis of the cathepsin G and carboxypeptidase B-degraded factor Xa

| Cycle no | Light chain (45-139), PTH-aa | Heavy chain, PTH-aa |
|---|---|---|
| 1 | Lys (K) | Ile (I) |
| 2 | Asp (D) | Val (V) |
| 3 | Gly (G) | Gly (G) |
| 4 | Asp (D) | Gly (G) |
| 5 | Gln (Q) | Gln (Q) |
| 6 | Cys* | Glu (E) |

*PTH-Cys is not determined

Characterization of the truncated factor Xa by SDS-PAGE and N-terminal amino acid sequence analysis reveals that cleavage after cathepsin G treatment had occurred at the light chain, between Tyr-44 and Lys-45. Moreover, treatment of factor Xa by carboxypeptidase B offers a convenient way of obtaining factor Xa deprived of Arginine at the C-terminal of the light chain. The success to modify the factor Xa molecule according to the statements above, will help us to determine the three dimensional structure of the protein

EXAMPLE 2

A solution of Human des-Gla factor Xa treated with carboxypeptidase to remove C-terminal Arg from the light chain, prepared in accordance with Example 1, comprising 20 mM Hepes, 50 mM ammonium sulfate and approximately 5.0 mg/ml of the truncated fXa was incubated for 1 hour with 2 mM of the Daiichi inhibitor DX-9065a ((2S)-(4-(1-acetimidoyl-(3S)-pyrrolidinyl)-oxyphenyl)-3-(7-amindino-2-naphtyl) propionic acid hydrochloride pentahydrate) prior to use in a crystallization experiment.

Crystallization

In order to obtain suitable crystals for X-ray analysis an extensive range of crystallization conditions have normally to be searched. Such a search for the best crystal growth conditions is a multi-dimensional problem in that there are many different variables to be taken into account such as the concentration of protein, buffer, precipitating agent and additives (e.g. detergents, salts, metal ions) in addition to the temperature and which crystallization method to use. All these have to be determined by trial and error as every protein has its own particular set of optimum crystal growth condition and unfortunately the results from one protein can not predictably be extrapolated to any other. In fact one can not even be certain a priori that any particular protein or protein complex can be crystallized under any conditions or even if crystals are obtained whether or not they will be suitable quality for X-ray analysis.

The crystals of the fXa-DX 90765a complex were grown using the standard method of hanging-drop vapor diffusion. Using this method, typically, 1 ml of a precipitation solution comprising 30% PEG 4000 and 0.2 M LiSO4, Tris pH 8.5 at a temperature of 20° C., is placed in the well of a plastic 24-well cell culture plate. A small volume (3 µl) of the precipitating solution is placed onto the surface of a siliconized glass cover-slip. An equal volume (3 µl) of the protein solution was then added to the precipitant drop. The cover-slip was then picked up using forceps and inverted over the cell-culture well. An air-tight seal is maintained between the well and the cover-slip by applying oil or silicon grease to the of the well. Over a period of time (from days to weeks) the concentration of the precipitant in the drop equilibrates with that in the well by diffusion via the vapor phase. As the concentration of the precipitant increases, the protein in the drop slowly becomes supersaturated and initiates the nucleation of protein crystals.

Characterization

A crystal grown according to the experiment above was drawn up into a quartz glass capillary tube (0.7 mm in diameter) from the drop in which it grew. After removing most of the fluid surrounding the crystal (mother liquid) with thin strips of filter paper, the capillary was sealed at both ends with wax and leaving a small reservoir of mother liquor at one end to prevent dehydration of the crystal. The capillary containing the crystal was then mounted on a goniometer head and fixed onto the camera of a MAR 30 cm Area Detector system in order to record the diffraction pattern on radiation of the crystal by X-rays. From the standard analysis of such X-ray diffraction images, it was determined that the above crystals have the orthorhombic space group P21 P21 P21, with the cell dimensions a=40.77 Å, b=77.64 Å, c=114.55 Å and $\alpha=\beta=\gamma=90°$, 1 molecule in the asymmetric unit and diffract to 2.7 Å resolution on our lab X-ray source.

Collection and processing of experimental data

In order to solve the atomic structure of molecules by X-ray crystallography, the positions and intensities of the diffraction maxima must be measured. The intensity data for the fXa-DX 9065a crystals was collected on a MAR 30 cm area-detector system. All data were obtained from a single crystal and processed initially with the DENZO software package. Merging and scaling of the data, however, was carried out using ROTAVATA and AGROVATA from the CCP4 package. The final data set contained 6653 independent reflections with and Rysm of 13.3% for all data between 20.0 and 3.0 Å resolution.

Solution of three-dimensional structure

The structure of the complex was solved by the standard method of molecular replacement using the program AMORE. The search model used was the refined 2.0 Å resolution structure of human fXa by Tulinsky et al. This model consisted of the catalytic heavy chain of fXa and single C-terminal epidermal growth factor (EGF) like domain of the light chain. The second Using 8.0 to 4.0 Å resolution data the top peak of the cross-rotation function gave the correct solution. The top peak in the translation function also gave correct solution. After the translation functions, the R-factor was 45.6% for 50.0 to 4.0 A resolution data. Subsequent rigid body refinement in which both domains of the fXa molecule in the asymmetric unit were allowed to refine independently resulted in an R-factor of 42.6% for the same data. Examination of the |Fo-|Fc electron density map at this stage using the graphics program O showed clear density corresponding to the inhibitor in the fXa active site. The orientation of the DX9065a inhibitor was easily determined from the electron density and was modeled into position.

Refinement and analysis of structure

Simulated annealing refinement with XPLOR was initiated at this stage. Several additional cycles of model building and refinement were carried out to yield an R-factor or the current model of 23% for 20.0 to 3.0 Å resolution data. The model at the present stage of refinement (which contains no water molecules and does nor contain the first N-terminal EGF domain) has root-mean square (rms) deviations from ideal geometry of 0.020 Å for bond lengths and 4.20 for bond angles.

EXAMPLE 3

The protein used is Des-Gla Factor Xa (treated with carboxypeptidase to remove Arg from C-terminus of the light chain) prepared in accordance with Example 1 in a solution comprising 20 mM HEPES, 50mM AmSO4, pH 8.0. Concentration approximately 5.0 mg/ml.

Crystallization:

The crystals of fXa without ligands were grown using the standard method of hanging-drop vapor diffusion. Using this method, typically, 1 ml of a precipitating solution is placed in the well of a plastic 24-well cell culture plate. A small volume (3 µl) of the precipitating solution was placed onto the surface of a siliconized glass cover-slip. An equal volume (3 µl) of the protein solution was then added to the precipitant drop. The cover slip was then picked up using forceps and inverted over the cell-culture well. An air-tight seal is maintained between the well and the cover slip by applying oil or silicon grease to the top of the well. Over a period of time (from days to weeks) the concentration of the precipitant in the drop equilibrates with that in the well by diffusion via the vapor phase. As the concentration of the precipitant increases the protein in the drop slowly becomes supersaturated and initiates the nucleation of protein crystals. The Precipitant solution used for crystallization was 25% PEG5000+0.2M (NH4)2SO4 0.1M HEPES pH 7.0 and the temperature was 18° C.

Characterization:

A crystal grown according to the experiment above was drawn up into a quartz glass capillary tube (0.7 mm in diameter) from the drop in which it grew. After removing most of the fluid surrounding the crystal (mother liquid) with thin strips of filter paper, the capillary was sealed at both ends with wax and leaving a small reservoir of mother liquor at one end to prevent dehydration of the crystal. The capillary containing the crystal was then mounted on a goniometer head and fixed onto the camera of a MAR 30 cm Area Detector system in order to record the diffraction pattern on radiation of the crystal by X-rays. From the standard analysis of such X-ray diffraction images, it was determined that the above crystals have the trigonal space group P3121, with the cell dimensions a=b=81.95 Å, c=108.76 Å, $\alpha=\beta=90°$ $\gamma=120.0°$, 1 molecule in the asymmetric unit and diffract to 2.9 Å resolution on our lab X-ray source.

Collection and processing of experimental data

In order to solve the atomic structure of molecules by X-ray crystallography, the positions and intensities of the diffraction maxima must be measured. The intensity data for the fXa crystals was collected on a MAR 30 cm area-detector system. All data were obtained from a single crystal and processed initially with the DENZO software package. Merging and scaling of the data, however, was carried out using ROTAVATA and AGROVATA from the CCP4 package. The final data set contained 5644 independent reflections with and Rysm of 19.1% for all data between 20.0 and 3.5 Å resolution.

Solution of three-dimensional structure

The structure of the complex was solved by the standard method of molecular replacement using the program AMORE. The search model used was the refined 2.0 Å resolution structure of human fXa by Tulinsky et al. This model consisted of the catalytic heavy chain of fXa and single C-terminal epidermal growth factor (EGF) like domain of the light chain. Using 8.0 to 3.5 Å resolution data the top peak of the cross-rotation function gave the correct solution. The top peak in the translation function also gave correct solution. After the translation functions, the R-factor was 40.9% for 50.0 to 3.5 Å resolution data. Subsequent rigid body refinement in which both domains of the fXa molecule in the asymmetric unit were allowed to refine independently resulted in an R-factor of 38.2% for the same data. Examination of the |Fo-|Fc electron density map at this stage using the graphics program O showed clearly that active site was empty.

We claim:

1. A modified factor Xa capable of forming crystals containing Epidermal Growth Factor (EGF)-like domains wherein a light protein chain of said modified factor is truncated in its N-terminal region and in its C-terminal region.

2. A modified factor Xa according to claim 1 deprived of its N-terminal gamma-carboxyglutamic acid containing region.

3. A modified factor Xa according to claim 1 deprived of its C-terminal amino acid.

4. A modified factor Xa according to claim 1 wherein the light chain has tryptophane (Trp) as a N-terminal amino acid.

5. A modified factor Xa according to claim 1 wherein the light chain has glutamic acid (Glu) as a C-terminal amino acid.

6. A modified factor Xa according to claim 1 being deprived of a polypeptide of about 40 amino acids in its N-terminal region.

7. A modified factor Xa according to claim 1 being deprived of its C-terminal arginine.

8. A method of preparing a modified factor Xa according to claim 1 characterized by enzymatically cleaving its light chain to remove a fragment in its N-terminal region and a fragment in its C-terminal region.

9. A method according to claim 8 wherein native factor Xa is subjected to enzymatic cleavage by the simultaneous activity of two different enzymes with specific protease activity.

10. A method according to claim 8, wherein the light chain is cleaved by cathepsin G to remove a fragment in its N-terminal region.

11. A method according to any of claim 8, wherein the light chain is cleaved by carboxypeptidase B to remove the C-terminal amino acid.

12. A method according to any of claim 8 characterized by (i) removing a polypeptide of 40 amino acids from the N-terminal end by cleaving with cathepsin G; and (ii) removing the C-terminal arginine by cleaving with carboxypeptidase.

13. Crystals of the modified factor Xa according to claim 1 without any ligand.

14. A modified factor Xa according to claim 1 being deprived of a polypeptide of about 44 amino acids from said N-terminal region.

* * * * *

UNITED STATES PATENT AND TRADEMARK OFFICE
CERTIFICATE OF CORRECTION

PATENT NO. : 6,069,234
DATED : May 30, 2000
INVENTOR(S) : Joanna Chmielewska, Tomas Lundqvist, Erifili Masialou, Derek Ogg It is certified that error appears in the above-identified patent and that said Letters Patent are hereby corrected as shown below:

Title page, item [73] Assignee:

Line 1, Delete "Pharmacia & Upjohn AB" and replace with "Axys Pharmaceuticals, Inc."

Signed and Sealed this

First Day of May, 2001

*Attest:*

NICHOLAS P. GODICI

*Attesting Officer*        *Acting Director of the United States Patent and Trademark Office*